United States Patent [19]

Smith

[11] Patent Number: 4,546,767
[45] Date of Patent: Oct. 15, 1985

[54] CEMENT INJECTION DEVICE

[76] Inventor: Carl W. Smith, 1317 W. 162nd St., Gardena, Calif. 90247

[21] Appl. No.: 546,199

[22] Filed: Oct. 27, 1983

[51] Int. Cl.⁴ .......................... A61F 5/04; A24F 25/00
[52] U.S. Cl. ................................ 128/92 E; 128/92 R; 604/224
[58] Field of Search .............. 128/92 R, 92 E, 303 R, 128/92 BC, 92 C; 604/208-210, 223-224

[56] References Cited

U.S. PATENT DOCUMENTS

| | | |
|---|---|---|
| 1,379,471 | 5/1921 | Mood . |
| 1,576,822 | 3/1926 | Hayden et al. . |
| 1,720,890 | 7/1929 | Fesler . |
| 3,223,083 | 12/1965 | Cobey ................................ 128/92 R |
| 3,732,872 | 5/1973 | Lakritz ................................ 604/224 |
| 3,741,204 | 6/1973 | Thiele ................................ 128/92 R |
| 3,889,665 | 6/1975 | Ling et al. .......................... 128/92 R |
| 3,913,799 | 10/1975 | Davis, Jr. .............................. 222/326 |
| 4,093,576 | 6/1978 | de Wijn ................................ 128/92 R |
| 4,277,184 | 7/1981 | Solomon ............................ 128/92 R |
| 4,338,925 | 7/1982 | Miller ................................ 128/92 E |
| 4,341,691 | 7/1982 | Anuta ................................ 128/92 R |
| 4,369,772 | 1/1983 | Miller ................................ 128/92 R |
| 4,399,814 | 8/1983 | Pratt, Jr. et al. ................. 128/92 R |
| 4,462,394 | 7/1984 | Jacobs ............................... 128/92 E |
| 4,494,535 | 1/1985 | Haig ................................... 128/92 R |
| 4,497,705 | 2/1985 | Niwa et al. ........................ 128/92 R |

Primary Examiner—Gene Mancene
Assistant Examiner—C. W. Shedd
Attorney, Agent, or Firm—Fulwider Patton Rieber Lee & Utecht

[57] ABSTRACT

A device for controlling the injection of a cement into a cavity is provided which is particularly useful in the practice of total hip arthroplasty. A canister holds a standard cement syringe and supports a retracting assembly which withdraws a nozzle of the syringe into the canister. The device ensures that the tip of the nozzle remains at or very near the meniscus of the rising cement column so that the cement flows primarily radially into the cavity by withdrawing the nozzle into the canister as the cement is injected. Additionally, a pressure release mechanism permits the syringe to migrate as a unit independently of the retracting assembly to maintain the tip of the nozzle at the meniscus of the rising cement column.

20 Claims, 9 Drawing Figures

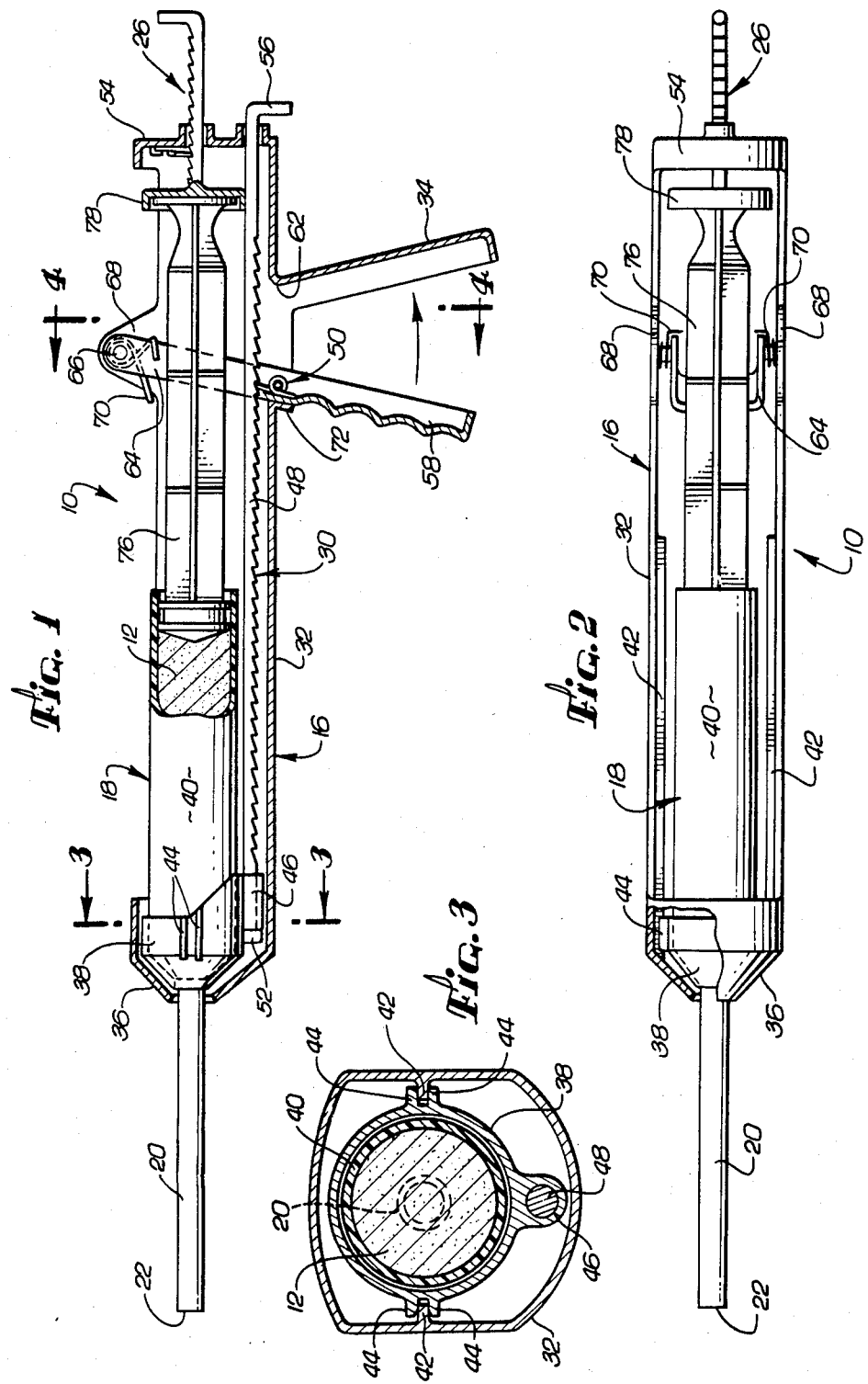

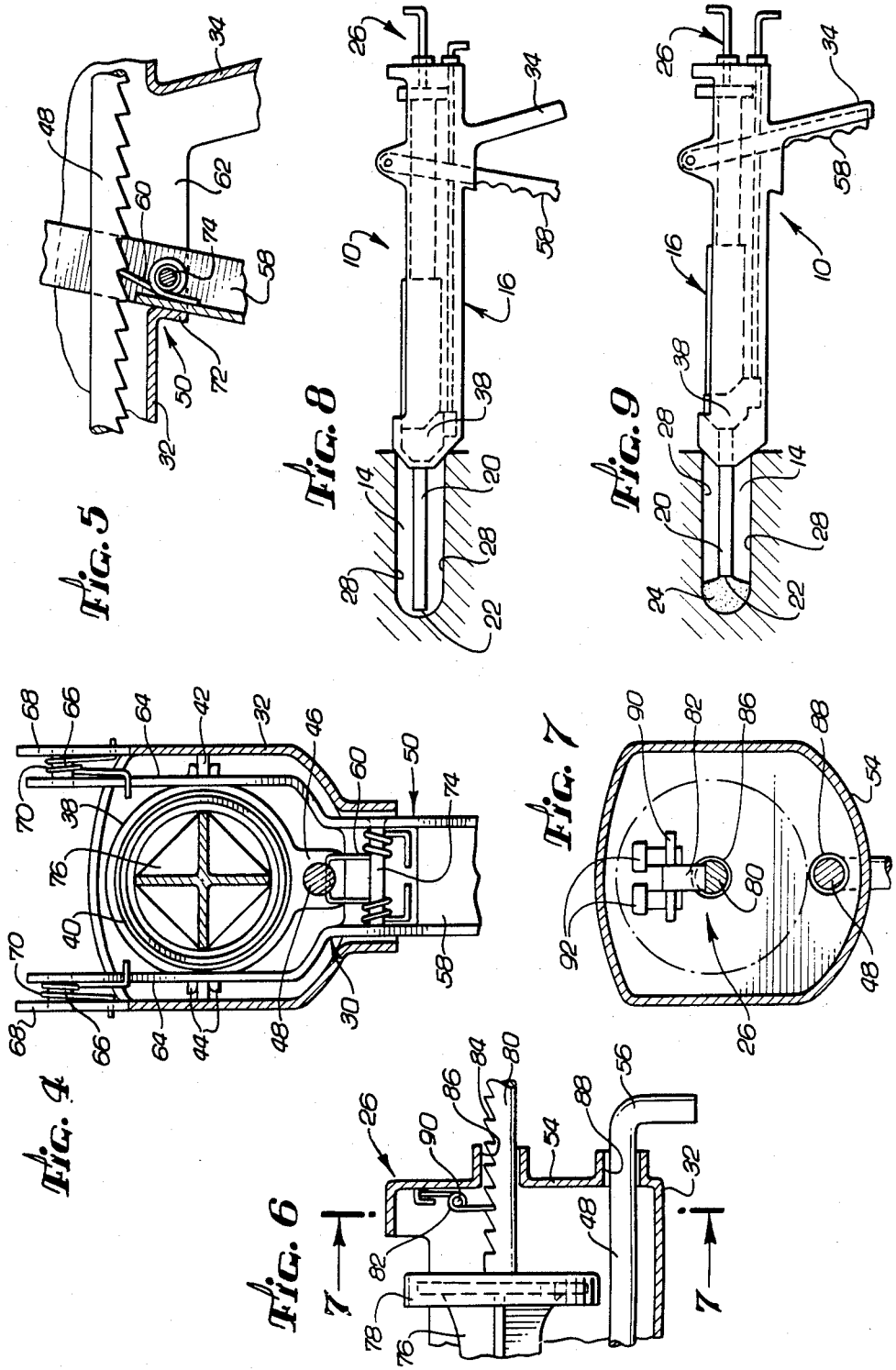

CEMENT INJECTION DEVICE

BACKGROUND OF THE INVENTION

The present invention relates to devices used for dispensing a viscus fluid, and, more particularly, to a device used for injecting a surgical cement into a cavity formed in a bone to secure a prosthesis such as the femoral component in a total hip arthroplasty.

Previously, when it was desirable to fill with a cement a relatively slender cylindrical cavity, the cement was simply poured through the cavity aperture or injected with a standard syringe. In the present practice of orthopedic surgery, a cavity is formed in a bone to receive a prosthetic bone component and a surgical cement is injected into the cavity using an enlarged conventional syringe. More particularly, in the practice of total hip arthroplasty a methyl methacrylate cement is injected into a femoral cavity to secure the femoral prosthesis component of the arthroplasty within the cavity.

Surgeons generally recognize that it is desirable to inject the surgical cement into the femoral cavity by inserting an elongated nozzle to the bottom and injecting the cement so that it flows from the center of the cavity radially to the cavity wall. Furthermore, the nozzle should be withdrawn steadily and continuously to keep the tip of the nozzle at or very near the meniscus of a rising cement column so that the flow of the cement continues to be primarily radial in nature.

Unfortunately, a common technique used by surgeons to inject the surgical cement into the femoral cavity is to use a large volume syringe, including an elongated nozzle, through which the surgeon injects the surgical cement while attempting to maintain the tip of the nozzle at the meniscus of the rising cement column. Since it is very difficult to see down into the femoral cavity during surgery, manual withdrawal of the syringe can only approximate an optimum rate which would maintain the tip at the meniscus and cause radial cement flow to the cavity wall. If the nozzle is retracted too slowly, its tip will fall below the meniscus of the cement and cause the cement to flow both radially and axially along the cavity walls, picking up debris along the rough cavity walls, and not achieving proper bone intrusion. If the nozzle is withdrawn too rapidly, the pressure of the injected cement is too low to achieve proper bone intrusion and air gaps may be formed detracting from the capability of the cement to hold the prosthesis firmly. The magnitude of the problems inherent in the improper injection of surgical cement during orthopedic surgeries is readily apparent when one realizes that such weakening of the cement bond often necessitates corrective surgery.

Accordingly, a device is needed for injecting the cement into the cavity while withdrawing the nozzle of the injection device automatically at the optimum rate for achieving the desired flow of the cement into the cavity and at the desired pressure. Such a device must eliminate the guess work attendant to prior techniques for injecting surgical cement and the device must have the capability to compensate for variations in cavity volumes. The present invention fulfills these needs and provides other related advantages.

SUMMARY OF THE INVENTION

The present invention resides in a novel cement injection device particularly useful in the practice of total hip arthroplasty to secure a femoral prosthesis component within a femoral cavity. Generally, the novel device includes a canister for holding a standard cement syringe which allows a nozzle connected to the syringe to extend from the canister. When the nozzle is inserted into the femoral cavity for injection of the cement, a portion of the canister contacts the femur processes and remains stationary with respect to the femur during injection. While the cement is being injected into the cavity, a retracting assembly attached to the canister withdraws the nozzle into the canister automatically at substantially the optimum rate for achieving the desired flow of the cement into the cavity.

In one preferred form, the retracting assembly includes a retractor, which moves along a track, and an anchor. To utilize the cement injection device, the standard cement syringe, having an internal major diameter equal to or slightly larger than the cavity to be filled, is placed within the canister. When so placed, a plunger of the syringe is held stationary with respect to the canister by the anchor and a barrel of the syringe is supported by the retractor. The device is positioned so that the tip of the nozzle is at the bottom of the cavity and a portion of the canister adjacent the retractor is situated over the cavity aperture allowing the canister to rest on the bone. When the retractor is drawn toward the anchor, the cement is injected and the nozzle is simultaneously withdrawn from the cavity into the stationary canister. Throughout the injection process, the cement injection device ensures that the tip of the nozzle remains at or very near the meniscus of the rising cement column so that the flow of the cement is primarily radial in nature.

Additionally, this device includes a pressure release mechanism designed to compensate for variations in femoral cavity volumes. If, during the injection process, the cavity fills more rapidly than the nozzle is being retracted, the release mechanism will sense an increasing pressure needed to inject the cement as the tip of the nozzle submerges below the more rapidly rising cement column. At a given pressure, the release mechanism will alow the nozzle, the barrel and the plunger to migrate as a unit in the direction of the nozzle retraction until the tip of the nozzle is again at the meniscus of the cement column. Once the tip of the nozzle has been correctly repositioned, the normal injection process is resumed.

Other features and advantages of the present invention will become apparent from the following more detailed description, taken in conjunction with the accompanying drawings, which illustrate, by way of example, the principles of the invention.

DESCRIPTION OF THE DRAWINGS

The accompanying drawings illustrate the invention. In such drawings:

FIG. 1 is an elevational view of a cement injection device embodying this invention with a canister, a trigger lever, and an anchor sectioned to illustrate an injection syringe which has its barrel partially broken away to more fully illustrate a syringe plunger;

FIG. 2 is a plan view of the cement injection device of FIG. 1, with a portion of the canister broken away to show a retractor;

FIG. 3 is an enlarged sectional view taken generally along the line 3—3 of FIG. 1;

FIG. 4 is an enlarged fragmentary sectional view taken generally along the line 4—4 of FIG. 1;

FIG. 5 is a fragmentary sectional elevational view of the cement injection device illustrating the relative positioning and interaction of a trigger pawl, a rachet rod and the canister;

FIG. 6 is a fragmentary sectional elevational view of the cement injection device, illustrating particularly the detail of a pressure release mechanism and its location relative to the canister and the ratchet rod;

FIG. 7 is a sectional view taken generally along the line 7—7 of FIG. 6;

FIG. 8 is an elevational schematic illustration of the cement injection device positioned over a cavity immediately prior to the injection of a cement;

FIG. 9 is an elevational schematic illustration similar to FIG. 8, further showing the syringe being retracted into the canister as the cement is injected into the cavity.

DETAILED DESCRIPTION OF THE PREFERRED EMBODIMENT

As shown in the drawings for purposes of illustration, the present invention is embodied in a cement injection device, referred to generally by the reference number 10, which controls the injection of a cement 12 into a cavity 14 (FIGS. 8 and 9). More particularly, the cement injection device 10 is especially useful to a surgeon for injecting a surgical cement into a femoral cavity during a total hip arthroplasty.

The cement injection device 10 includes a canister 16 which supports a standard syringe 18 including an elongated nozzle 20. In accordance with the present invention, the device 10 is designed to overcome the problems inherent in present injection techniques by providing a device for withdrawing a tip 22 of the nozzle 20 as the cement 12 is injected into the cavity 14 so that the tip remains at the meniscus of a rising cement column 24. The cement injection device 10 ensures a steady and uniform application of the cement 12 from the distal portion of the cavity 14 to the cavity's aperture. Additionally, a pressure release mechanism 26 is provided to automatically compensate for variations in cavity volumes. Use of this novel device 10 minimizes the mixing of debris with the cement 12 and enhances the proper application of the cement to the cavity walls 28 to assure proper bonding.

As illustrated in FIGS. 1 and 2, the cement injection device 10 generally comprises the canister 16 which supports the cement-bearing syringe 18 therein, and a retracting assembly 30 which moves the syringe within the canister.

The canister 16 includes a body 32 which either houses or supports all of the other elements comprising the cement injection device 10 and a handle 34. A truncated conical nose section of the canister 16 is integrally attached to the front of the canister body 32 to form a canister support seal rim 36. This canister support seal rim 36 rests against the area surrounding the cavity aperture while the cement 12 is being injected into the cavity 14 to form a seal thereabout preventing the entrance into the cavity of material which could interfere with the bonding process between the cavity walls 28 and the cement. More specifically, during a total hip arthroplasty the canister support seal rim 36 would be placed over the femoral cavity so that the seal rim rested upon the femoral processes to form a seal preventing the entrance of body fluids or other materials into the femoral cavity during the cement injection process.

Comprising a portion of the retracting assembly 30 is a syringe retractor 38, partially enclosed by the canister body 32, which is designed to support a barrel portion 40 of the syringe 18 while allowing the nozzle 20 to extend therefrom. As illustrated in FIG. 3, the syringe barrel 40 adjacent the nozzle 20 is supported within the retractor 38 so that the nozzle extends through the retractor as well as the canister support seal rim 36. The retractor 38 is positioned within the canister 16 by two canister tracks 42 which interact with channel-like retractor guides 44 to guide the retractor along a restricted travel path through the canister body 32. A rachet rod support housing 46 is also included as part of the retractor 38 to provide a point of attachment for a rachet rod 48 so that it can force the retractor rearwardly, or away from the canister support seal rim 36, through the canister body 32.

As shown in FIGS. 1, 4 and 5, this rachet rod 48 is included in the retracting assembly 30 and it interacts with a rachet trigger 50 to rearwardly pull the retractor 38 through the canister body 32. The rachet rod 48 comprises a long rod having a toothed mid-section and generally cylindrical end sections. A front end of the rachet rod 48 fits within the rachet rod support housing 46 and is capped by an enlarged or mushroomed portion 52 to fasten the rod to the retractor 58 while allowing the rod to rotate within the housing. The opposite end of the rachet rod 48 extends through a base 54 of the cannister 16 in a manner allowing this section of the rod to rotate also. The section of the rod 48 extending through the base 54 includes an angled or bent portion 56 to provide a type of handle allowing an operator to readily rotate the rod as desired.

The rachet trigger 50 generally includes a trigger lever 58 which supports a rachet pawl 60. Shown best in FIG. 4, the trigger lever 58 enters the canister body 32 through a bottom opening 62 and splits into two trigger yokes 64 which bracket the syringe 18 being carried by the canister 16. These trigger yokes 64 are rotatably connected by a pair of hinges 66 to the canister 16 at two hinge supports 68. Springs 70 are threaded onto the hinges 66 and positioned to force the trigger lever 58 toward the front of the injection device 10 so that the trigger lever rests against an abutment 72 defining a portion of the bottom opening 62 (FIGS. 1 and 5).

The rachet pawl 60 is essentially a spring mounted upon a shaft 74 which is supported by the trigger lever 58. The pawl 60 is positioned so that it can engage the teeth of the rachet rod 48 and drive the rachet rod rearwardly when the lever 58 is pulled in that direction. Similarly, the ratchet pawl 60 is tensioned so that as the lever 58 moves forward under the influence of the trigger hinge springs 70, the pawl deflects over the rachet rod 48 teeth (FIG. 5). The pawl may also be selectively engaged or disengaged from the rachet rod 48 by simply rotating the rod 90 degrees. This feature specifically allows the retractor 38 to be repositioned within the canister body 32 as desired.

The syringe 18, comprising the nozzle 20, the barrel 40 and a plunger 76, has an internal major barrel diameter equal to or slightly larger than the cavity 14. When the syringe 18 is filled with the cement 12 and placed within the canister 16 so that the syringe barrel 40 is supported by the retractor 38 and the plunger 76 is supported by an anchor 78, the cement injection device 10 is read for operation. As illustrated in FIGS. 8 and 9, the canister support seal rim 36 is positioned over the cavity 14 so that the cavity is covered and sealed by the seal rim. The rachet rod 48 should position the retractor 38 so that the tip 22 of the nozzle 20 extends to the bottom of the cavity 14 and the nozzle should be primed so that any rearward movement of the lever 58 will immediately cause the cement 12 to be injected. The operator would normally grasp the canister body 32 with one hand and the handle 34 with the other to hold the device 10 stationary over the cavity 14 throughout the injection process.

As the trigger lever 58 is rotated toward the handle 34, the rachet pawl 60 engages the rachet rod 48 and forces it rearwardly, pulling the retractor 38 along with it. Because the retractor 38 houses the syringe barrel 40 the retractor forces the syringe barrel over the plunger 76 and thus forces the cement 12 to be expelled through the nozzle 20 into the cavity 14. The movement of the retractor 38 likewise withdraws the nozzle 20 from the cavity 14 and into the cannister 16 with the effect of maintaining the tip 22 of the nozzle at the meniscus of the rising cement column 24.

The handle 34 limits the rearward movement of the trigger lever 58. Whenever the operator releases the trigger lever 58, the hinge springs 70 cause the lever to rotate back to its initial position without disturbing the positioning of the syringe 18, and more particularly the nozzle 20. The process of rotating the lever 58 rearwardly and then releasing the same may be repeated until the nozzle 20 is completely withdrawn from the cavity 14 and throughout this process the device 10 will ensure that the tip 22 is maintained at the meniscus of the rising cement column 24.

If the cavity 14 fills more rapidly than the nozzle 20 is retracted, the pressure release mechanism 26 will sense the increasing pressure in the system needed to inject the cement 12 as the tip 22 submerges below the more rapidly rising cement column 24. At a given pressure, this mechanism 26 will release and allow the nozzle 20, the syringe barrel 40 and the plunger 76 to migrate as a unit in the direction of nozzle retraction (rearwardly). This will slow the injection flow of the cement 12 but still allow for nozzle retraction to maintain the nozzle 20 at the meniscus of the cement column 24.

As best illustrated in FIGS. 6 and 7, the pressure release mechanism 26 attaches to and supports the anchor 78 in a manner that permits the anchor to move rearwardly when the tip 22 of the nozzle submerges below the meniscus of the cement column 24. The release mechanism generally comprises a toothed release rod 80 and a release spring 82.

The release rod 80 is attached at one end to the anchor 78 which supports the plunger 76. The teeth of the release rod 80 are typically oriented in an opposite manner than the teeth of the rachet rod 48 in that the release rod teeth face upwardly with rearward holding faces 84. A release rod sleeve 86, which is similar to a rachet rod sleeve 88, is provided in the canister base 54, to permit the release rod 80 to extend therethrough so that it can be grasped and rotated by the operator to position the anchor 78 as required by the size of the syringe 18 used and the cavity 14 to be injected.

The release spring 82 is mounted upon a release spring hinge 90 attached to the canister base 54. One end of the release spring 82 is fastened to the canister base 54 by two brackets 92. The other end of the release spring 82 interacts with the teeth of the release rod 80 to prevent the rod's displacement during the injection process unless the tip 22 submerges below the meniscus of the cement column 24. The size of the release spring is determined by utilizing known methods with respect to the viscosity of the cement 12 being injected.

Should the tip 22 of the nozzle 20 submerge below the meniscus of the rapidly rising cement column 24, the pressure exerted on the nozzle will be transmitted through the syringe 18 to the anchor 78 and finally to the pressure release mechanism 26. As the pressure increases, the release spring 82 will deflect rearwardly until one or more of the teeth of the release rod 80 are allowed to pass. By providing for movement of the anchor 78, the pressure release mechanism 26 permits the nozzle 20 to be retracted within the canister 16 sufficiently to replace the tip 22 at the meniscus of the cement column 24 without the injection of additional cement 12. When the pressure is no longer sufficient to fully deflect the release spring 82, the spring interacts with the release rod 80 to rigidly hold the anchor 78 in place. Thereafter, the movement of the syringe 18 is caused only by the action of the rachet rod 48 pulling on the retractor 38 which in turn causes the syringe barrel 40 to slide over the stationary plunger 76.

Although the illustrated cement injection device 10 uses a retracting assembly 30 whereby the retractor 38 is pulled by a rachet rod 48 by using a squeeze-handle trigger 58, this device may easily be modified for use with a powered gun (not shown) which uses a threaded drive rod.

The novel cement injection device 10 disclosed herein provided an apparatus capable of automatically withdrawing the nozzle 20 of the syringe 18 at the optimum rate for cement injection by maintaining the tip 22 at the meniscus of the rising cement column 24 within the cavity 14. This device eliminates the guess work attendant to prior injection techniques and it has the capability to adjust for variations in cavity volumes. Surgeons performing a total hip arthroplasty will find this device particularly useful for injecting a surgical cement into a femoral cavity to secure a femoral prosthesis component therein because the cement injection device 10 enhances the probabilities of a strong bond being formed between the femur and the cement 12.

Although a particular embodiment of the invention has been described in detail for purposes of illustration, various modifications may be made without departing from the spirit and scope of the invention. Accordingly the invention is not to be limited, except as by the appended claims.

I claim:

1. A device for injecting a cement into a cavity, comprising:
    a syringe including a barrel for holding the cement and a plunger;
    a nozzle attached to and extending from said barrel so that the cement held in said barrel passes through said nozzle for injection into the cavity;
    a canister for supporting said syringe which allows said nozzle to extend through and outwardly from said canister;
    means for withdrawing said nozzle into said canister while simultaneously expelling the cement from said barrel through said nozzle for injection into the cavity; and
    means for compensating for variations in the volumes of the cavities, said compensating means permitting the movement of said syringe and said nozzle as a unit to maintain a tip of said nozzle at the meniscus of a rising column of the injected cement.

2. A device according to claim 1 including a cavity seal forming the portion of said canister surrounding said nozzle, said seal preventing the entrance of foreign substances into the cavity while the cement is being injected therein.

3. A device according to claim 1 wherein said withdrawing means comprises:
- a retractor which receives said nozzle therethrough and provides support for a portion of said barrel adjacent said nozzle;
- an anchor for substantially rigidly supporting said plunger; and
- a mechanism for positively engaging and forcefully displacing said retractor toward said anchor thereby causing said nozzle to withdraw from the cavity into said canister.

4. A device according to claim 3 including means for guiding said retractor along a predetermined pathway as said retractor travels through said canister toward said anchor.

5. A device for injecting a cement into a cavity, comprising:
- a syringe including a barrel for holding the cement and a plunger;
- a nozzle attached to an extending from said barrel so that the cement held in said barrel passes through said nozzle for injection into the cavity;
- a canister for supporting said syringe which allows said nozzle to extend through said canister;
- means for withdrawing said nozzle into said canister while simultaneously expelling the cement from said barrel through said nozzle for injection into the cavity; and
- a cavity seal surrounding said nozzle, said seal preventing the entrance of foreign substances into the cavity while the cement is being injected therein.

6. A device according to claim 5 including means for compensting for variations in the volume of the cavity, said compensating means permitting the movement of said syringe and said nozzle as a unit to maintain a tip of said nozzle at the meniscus of a rising column of the injected cement.

7. A device according to claim 5 wherein said withdrawing means comprises:
- a retractor which receives said nozzle therethrough and provides support for a portion of said barrel adjacent said nozzle;
- an anchor for substantially rigidly supporting said plunger; and
- a mechanism for positively engaging and forcefully displacing said retractor toward said anchor thereby causing said nozzle to withdraw from the cavity into said canister.

8. A device according to claim 7 including means for guiding said retractor along a predetermined pathway as said retractor travels through said canister toward said anchor.

9. A device for injecting a cement into a cavity, comprising:
- a syringe including a barrel for holding the cement and a plunger;
- a nozzle attached to and extending from said barrel so that the cement held in said barrel passes through said nozzle for injection into the cavity;
- a canister for supporting said syringe which allows said nozzle to extend through and outwardly from said canister; and
- means for withdrawing said nozzle into said canister while simultaneously expelling the cement from said barrel through said nozzle for injection into the cavity.

10. A device according to claim 9 including a cavity seal surrounding said nozzle, said seal preventing the entrance of foreign substances into the cavity while the cement is being injected therein.

11. A device according to claim 9 including means for compensating for variations in the volume of the cavity, said compensating means permitting the movement of said syringe and said nozzle as a unit to maintain a tip of said nozzle at the meniscus of a rising column of the injected cement.

12. A device according to claim 9 wherein said withdrawing means comprises:
- a retractor which receivs said nozzle therethrough and provides support for a portion of said barrel adjacent said nozzle;
- an anchor for substantially rigidly supporting said plunger; and
- a mechanism for positively engaging and forcefully displacing said retractor toward said anchor thereby causing said nozzle to withdraw from the cavity into said canister.

13. A device according to claim 12 including means for guiding said retractor along a predetermined pathway as said retractor travels through said canister toward said anchor.

14. A device for injecting a surgical cement into a femoral cavity, said device comprising:
- a syringe including a plunger, a nozzle, and a barrel for holding the cement prior to its injection into the femoral cavity;
- a canister which supports said syringe therein and which allows said nozzle to extend through and outwardly from said canister;
- a cavity seal surrounding said nozzle, said seal preventing the entrance of foreign substances into the femoral cavity while the surgical cement is being injected therein;
- means for withdrawing said nozzle into said canister while simultaneously expelling the cement from said barrel through said nozzle for injection into the femoral cavity; and
- means for compensating for variations in the volume of the cavity, said compensating means permitting the movement of said syringe as a unit to maintain a tip of said nozzle at the meniscus of a rising column of the injected surgical cement.

15. A device according to claim 14 wherein said withdrawing means comprises:
- a retractor which receives said nozzle therethrough and provides support for a portion of said barrel adjacent said nozzle;
- an anchor for substantially rigidly supporting said plunger; and
- a mechanism for positively engaging and forcefully displacing said retractor toward said anchor thereby causing said nozzle to withdraw from the cavity into said canister.

16. A device according to claim 15 including means for guiding said retractor along a predetermined pathway as said retractor travels through said canister toward said anchor.

17. A method of injecting a surgical cement into a cavity, the steps comprising:

placing a cement injection device over a cavity aperture so that a canister of said device covers said aperture and rests against a surface surrounding said aperture and a nozzle of said device extends to the bottom of the cavity;

ensuring that after said device is so placed, said canister remains stationary with respect to the cavity during injection;

withdrawing said nozzle from the cavity and into said canister while simultaneously injecting the cement into the cavity through said nozzle; and maintaining a tip of said nozzle at the meniscus of a rising column of the injected cement to ensure primarily radial flow of the injected cement from said tip to the cavity walls.

18. A method according to claim 17 including the step of sealing said aperture with said cement injection device to prevent the entrance of substances into the cavity which could interfere with the bone intrusion of the surgical cement.

19. A method of injecting a surgical cement into a femoral cavity during a total hip arthroplasty, the steps comprising:

providing a cement bearing syringe, including an elongated nozzle; said syringe having a cross-sectional barrel area equal to or slightly larger than the average cross-sectional area of the cavity;

loading said syringe into a cement injection device, allowing said nozzle to protrude therethrough and extend therefrom;

placing said injection device over the cavity aperture so that said nozzle extends through the length of the cavity to the bottom thereof and said device substantially covers the aperture and rests against the femur processes;

ensuring that after said device is so placed, said device remains stationary with respect to the femur during injection;

withdrawing said nozzle from the femoral cavity and into said injection device while simultaneously injecting the surgical cement into the femoral cavity through said nozzle; and maintaining a tip of said nozzle at the meniscus of a rising column of the injected cement to ensure primarily radial flow of the injected surgical cement from said tip to the cavity walls.

20. A method according to claim 19 including the step of sealing the aperture with said cement injection device to prevent the entrance of substances into the femoral cavity which could interfere with intrusion of the cement into the femoral cavity walls.

* * * * *